(12) United States Patent
Hunter, Jr.

(10) Patent No.: US 10,940,071 B1
(45) Date of Patent: Mar. 9, 2021

(54) LATERAL POSITIONER FOR ELBOW SURGERY

(71) Applicant: Hunter Medical, LLC, Columbia, TN (US)

(72) Inventor: Alton Lee Hunter, Jr., Columbia, TN (US)

(73) Assignee: Hunter Medical, LLC, Franklin, TN (US)

( * ) Notice: Subject to any disclaimer, the term of this patent is extended or adjusted under 35 U.S.C. 154(b) by 568 days.

(21) Appl. No.: 15/729,432

(22) Filed: Oct. 10, 2017

Related U.S. Application Data

(60) Division of application No. 14/268,989, filed on May 2, 2014, now Pat. No. 9,782,318, which is a continuation-in-part of application No. 13/717,352, filed on Dec. 17, 2012, now Pat. No. 9,271,862, which is a continuation of application No. 13/087,841, filed on Apr. 15, 2011, now Pat. No. 8,356,601, which is a continuation-in-part of application No. 12/550,701, filed on Aug. 31, 2009, now Pat. No. 8,230,864.

(51) Int. Cl.
*A61G 13/12* (2006.01)
*A61F 5/37* (2006.01)

(52) U.S. Cl.
CPC ........ *A61G 13/1235* (2013.01); *A61F 5/3761* (2013.01); *A61G 13/124* (2013.01); *A61G 13/129* (2013.01); *A61G 2210/10* (2013.01); *A61G 2210/50* (2013.01)

(58) Field of Classification Search
CPC .. A61G 13/1235; A61G 13/124; A61G 7/075; A61G 13/122; A61G 13/1255; A61G 1/044; A61G 13/129; A61G 2210/10; A61G 2210/50; A61G 13/00; A61G 15/00; A61F 5/3761; A61F 5/00; A61B 6/04

See application file for complete search history.

(56) References Cited

U.S. PATENT DOCUMENTS 988,923 A * 4/1911 Bauerfeind ........ A61G 13/1235
  5/646
473,200 A 4/1982 Streeter
(Continued)

FOREIGN PATENT DOCUMENTS

FR 2578417 A1 9/1986

OTHER PUBLICATIONS

U.S. Appl. No. 14/268,989, filed May 2, 2014, Hunter.
(Continued)

*Primary Examiner* — Ophelia A Hawthorne
(74) *Attorney, Agent, or Firm* — Waller Lansden Dortch & Davis, LLP; Matthew C. Cox

(57) ABSTRACT

A device for supporting a patient's arm includes a rail clamp configured to be secured to a rail or other structure on a table such as an operating table. The rail clamp includes a clamp body and a socket configured to receive a base on an attachment such as a lateral brace. The base may be inserted longitudinally in the longitudinal socket on the rail clamp. The base may comprise an arm brace. The base is moveable in the longitudinal socket such that the arm brace may be raised or lowered relative to the rail clamp. The arm brace may be used when a patient is lying prone or laterally on a table.

19 Claims, 17 Drawing Sheets

(56) References Cited

U.S. PATENT DOCUMENTS

| | | | |
|---|---|---|---|
| 4,373,709 A * | 2/1983 | Whitt | A61G 13/12 |
| | | | 128/882 |
| 5,462,247 A * | 10/1995 | Aldrich | A47B 21/0371 |
| | | | 248/118 |
| 5,537,702 A | 7/1996 | Brown-Milants et al. | |
| 5,785,057 A | 7/1998 | Fischer | |
| 5,884,974 A * | 3/1999 | Bergsten | A47B 21/0371 |
| | | | 297/411.35 |
| 5,904,655 A | 5/1999 | Brackett | |
| 5,961,512 A | 10/1999 | Purnell | |
| 6,467,487 B1 | 10/2002 | Rios | |
| 6,533,744 B1 | 3/2003 | Stanish et al. | |
| 6,629,944 B2 | 10/2003 | Smart | |
| 6,758,827 B2 | 7/2004 | Moss | |
| 7,017,215 B1 | 3/2006 | Singer et al. | |
| 7,143,458 B2 | 12/2006 | Slater, Jr. | |
| 7,441,293 B1 | 10/2008 | Singer et al. | |
| 7,634,828 B2 | 12/2009 | Elhabashy | |
| 7,686,775 B2 | 3/2010 | Branch | |
| 7,771,378 B2 | 8/2010 | Price et al. | |
| 7,832,035 B2 | 11/2010 | Walczyk | |
| 8,230,864 B2 | 7/2012 | Hunter | |
| 8,273,043 B2 | 9/2012 | Bonutti et al. | |
| 8,286,283 B2 | 10/2012 | Copeland et al. | |
| 8,356,601 B2 | 1/2013 | Hunter | |
| 8,545,373 B2 | 10/2013 | Borden | |
| 9,271,862 B2 | 1/2016 | Hunter | |
| 2002/0128577 A1 | 9/2002 | Smart | |
| 2005/0251076 A1 | 11/2005 | Branch | |
| 2008/0034502 A1 | 2/2008 | Copeland et al. | |
| 2008/0172791 A1 | 7/2008 | Walczyk | |
| 2008/0301878 A1 | 12/2008 | Elhabashy | |
| 2011/0048428 A1 | 3/2011 | Hunter, Jr. | |

OTHER PUBLICATIONS

Schure Med, 2016 Patient Positioning Catalog, 37 pages, dated Jan. 2016.
Allen Medical, Orthopaedics Catalog, 31 pages, dated Sep. 2016.
ACUMED, Arc Wrist Tower, 12 pages, dated Jan. 2009.
Smith & Nephew, TENET Medical Engineering,Tenet Wrist Tower, 4 pages, dated Sep. 2009.

\* cited by examiner

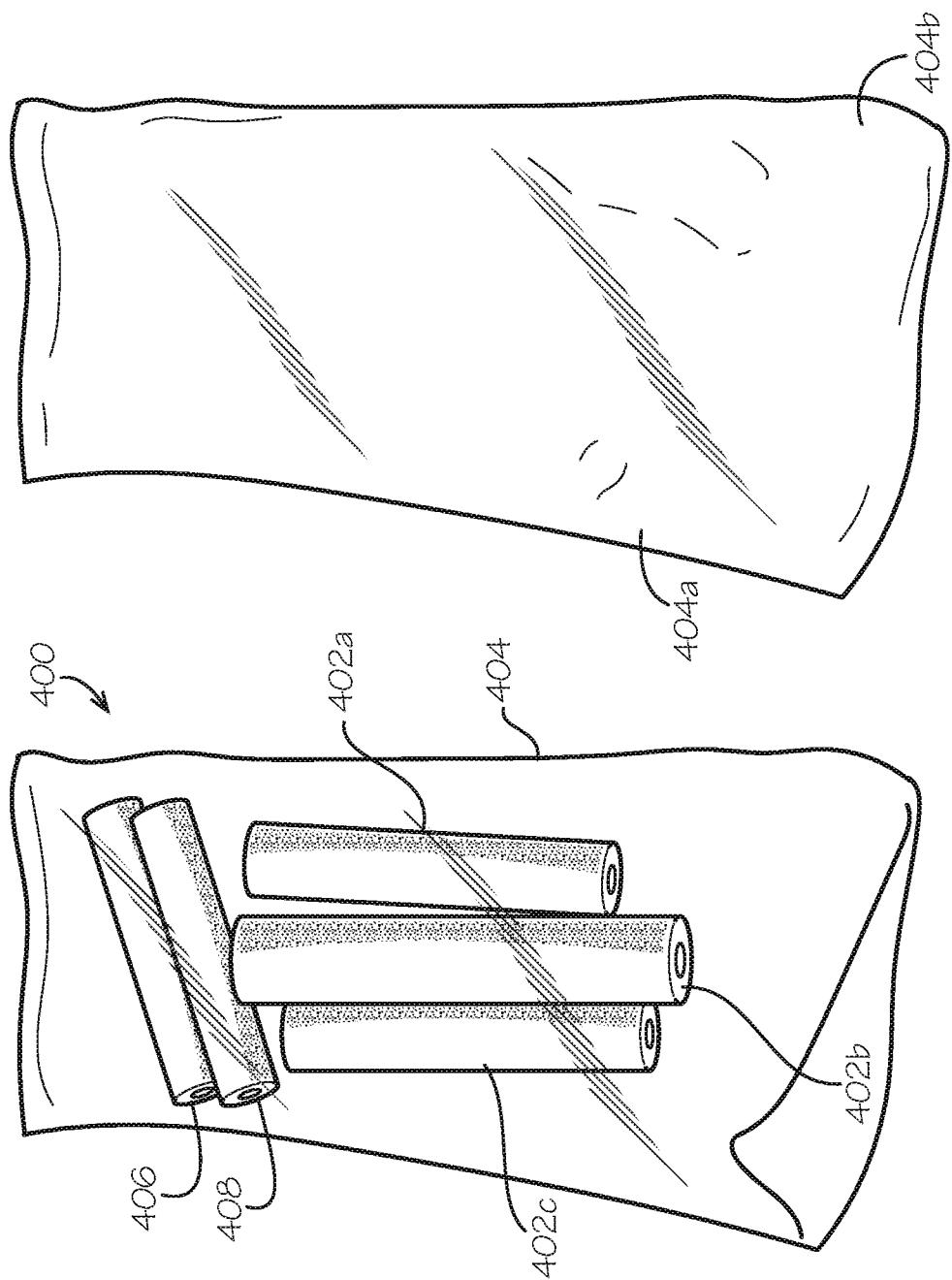

LATERAL POSITIONER FOR ELBOW SURGERY

CROSS-REFERENCES TO RELATED APPLICATIONS

This application is a divisional of co-pending U.S. patent application Ser. No. 14/268,989 filed May 2, 2014 entitled ARM STABILIZER DEVICE AND METHODS, which is a continuation-in-part of U.S. patent application Ser. No. 13/717,352 (now U.S. Pat. No. 9,271,862) filed Dec. 17, 2012 entitled "ARM STABILIZER DEVICE AND METHOD" which is a continuation of U.S. patent application Ser. No. 13/087,841 (now U.S. Pat. No. 8,356,601), filed Apr. 15, 2011, entitled "ARM STABILIZER DEVICE AND METHODS" which is a continuation-in-part of U.S. patent application Ser. No. 12/550,701 (now U.S. Pat. No. 8,230,864) filed Aug. 31, 2009 ; entitled "ARM STABILIZER FOR ELBOW SURGICAL PROCEDURE", all of which are herein incorporated by reference in their entireties.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present invention relates generally to orthopedic positioning devices and more particularly to devices and methods for supporting an arm before, during or after a surgical, rehabilitative or imaging procedure.

Surgical procedures on the extremities of humans occur with great frequency, and particularly surgeries on the arm, elbow, and hand. Injuries to a person's arm, elbow and hand come frequently from falls, reaching to catch one's self, slipping or landing on an elbow causing a shattering or dislocation of the bone structure within the elbow, and attempting to brace oneself in response to a fall resulting in fractured bones in the humerus, elbow, forearm, and/or hand.

During the course of procedures to repair the broken bones or other features in the arm, historically, the patient's arm has been placed on a pillow or some other support structure resting on the patient's waist or chest, or a foam pad can be used to support the arm. This procedure fails to properly secure and maintain in a fixed position the extremity on which the procedure is being conducted. There have been numerous attempts to address this problem, including those described and illustrated in U.S. Pat. Nos. 473,200; 5,785,057; 7,017,215; 7,143,458; 7,441,293 and U.S. Publication No. 2008/0301878. The prior devices that are available in the industry, including those described in the aforesaid patents are an improvement over the simple use of a pillow resting on the patient's chest, but remain inadequate. Specifically, conventional products fail to provide good exposure to the extremity, particularly to the patient's elbow, and make it difficult for the surgeon and assistants to have easy, unfettered access to the patient's elbow to properly complete the surgical, rehabilitative or imaging procedure. Additionally, conventional support devices do not allow vertical or longitudinal adjustment of a stabilizer bar and other modular attachments for the support device. Other support devices also generally do not allow interchangeability of different modular components for supporting different parts of the arm in different positions. Thus, there is a continuing need in the art for improvements in devices and methods for supporting an arm for such purposes.

BRIEF SUMMARY

The present invention generally provides devices and associated methods for stabilizing an arm during a surgical or rehabilitative procedure, during resting, during medical imaging of the arm, or during other times when it is desirable to have an arm stabilized in a stationary position.

In some embodiments, the present invention provides a rail clamp for attachment to a rail or other structure on a patient table such as an operating or surgical table. One or more attachments can be detachably secured to the rail clamp. Each attachment is also included as a part of the invention.

In further embodiments, the present invention provides an arm positioner including a rail clamp configured to be secured to a rail on a patient table and an arm support securable to the rail clamp. The arm support includes a stabilizer bar and a base in some embodiments. The base is configured to secure to the rail clamp such that the stabilizer bar extends away from the rail clamp. One or more attachments can be detachably secured to the stabilizer bar. The base includes a rod that slides vertically into a corresponding socket in the rail clamp in some embodiments.

A humeral support attachment is also detachably secured to the rail clamp in some embodiments to further support a patient's humeral region during use. The humeral support attachment includes a humeral support mount that engages and secures to the rail clamp and a humeral support bar extending from the humeral support mount in a direction away from the rail clamp. The humeral support bar provides support to a patient's humeral region during use. One or more humeral support pads may be positioned on the humeral support bar to pad a patient's arm during use.

A reducer attachment is also detachably secured to the stabilizer bar in some embodiments. The reducer attachment includes a reducer mount that engages and secures to the stabilizer bar in some embodiments. A reducer support bar extends from the reducer attachment mount generally away from the stabilizer bar to provide a support for a patient's arm during use.

A wrist support attachment is also detachably secured to the stabilizer bar in some embodiments. The wrist support attachment includes a wrist support mount configured to engage and secure to the stabilizer bar. A wrist support bar extends from the wrist support mount in a direction generally away from the stabilizer bar. The wrist support bar is configured to support the wrist region of a patient's arm during use.

Each attachment is provided in a modular arrangement such that the overall arm positioner device may be used with one or more of the modular attachments.

In further embodiments, a lateral positioner device includes a rail clamp including a lateral brace installed on the rail clamp. The lateral positioner device includes a lateral support post configured to engage the rail clamp. A lateral brace is disposed on the lateral support post. In some embodiments, the lateral support post slides into a corresponding socket on the rail clamp to secure the post to the rail clamp. The lateral brace is interchangeable with the arm support on the rail clamp in some embodiments.

Numerous other objects, features and advantages of the present invention will be readily apparent to those skilled in the art upon a reading of the following disclosure when taken in conjunction with the accompanying drawings.

BRIEF DESCRIPTION OF THE DRAWINGS

FIG. 17 illustrates a top view of an embodiment of a pad kit for use with an arm positioner or lateral positioner in accordance with the present disclosure.

FIG. 18 illustrates a top view of an enclosure for the pad kit of FIG. 17.

FIG. 19 illustrates a partial exploded view of the pad kit of FIG. 17.

DETAILED DESCRIPTION

Figure 1:
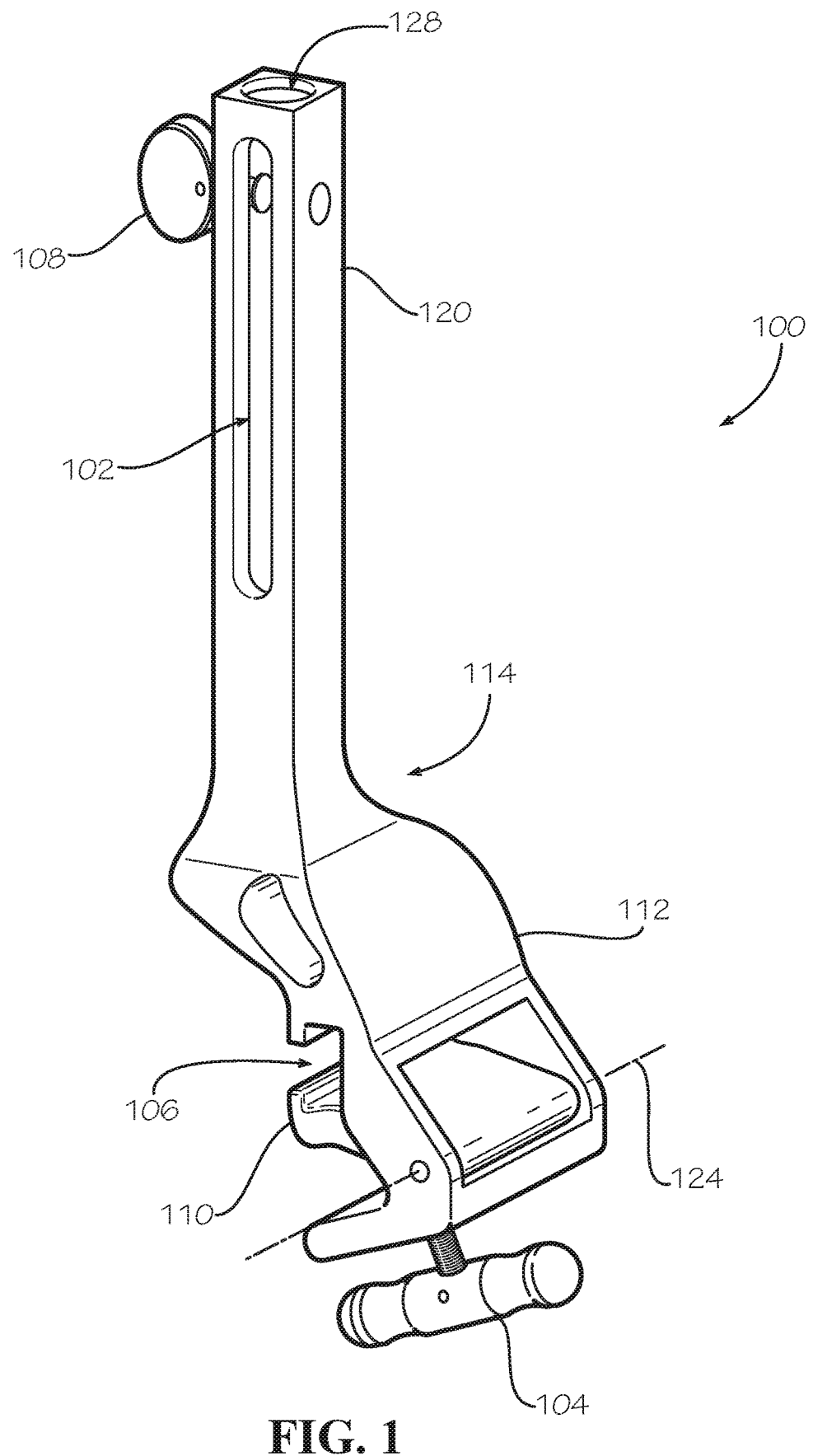
FIG. 1 illustrates a perspective view of an embodiment of a rail clamp in accordance with the present disclosure.

Referring now to the drawings, FIG. 1 illustrates a perspective view of an embodiment of an arm stabilizer generally designated by the numeral 10. In the drawings, not all reference numbers are included in each drawing, for the sake of clarity. In addition, positional terms such as "upper," "lower," "side," "top," "bottom," "vertical," "horizontal" etc. refer to the apparatus when in the orientation shown in the drawings or similar orientations. A person of skill in the art will recognize that the apparatus can assume different orientations when in use.

Referring further to FIG. 1, an embodiment of a rail clamp 100 in accordance with the present disclosure is generally illustrated. Rail clamp 100 is generally configured for attachment to a side rail or other similar structure on a table such as an operating table or a surgical table. Similar types of rails may be found on other structures for supporting or transporting patients. Rails of this nature include a universal mounting configuration in some applications to allow for interchangeability of attachments. Rail clamp 100 includes a clamp base 112 having a clamp jaw 110, or pawl, that is hinged about a pawl axis 124 on the clamp base 112. A mounting recess 106 is defined between clamp base 112 and clamp jaw 110 shaped to receive the rail on which rail clamp 100 is to be mounted. A rail clamp fastener 104 allows clamp jaw 110 to be tightened against the rail. A handle is positioned on the rail clamp fastener 104 to allow for manual adjustment of the force applied to clamp jaw 110.

Rail clamp 100 may be positioned along the longitudinal length of a rail 24 by simply loosening the rail clamp fastener 104, repositioning the rail clamp 100, and then re-tightening the rail clamp fastener 104. This allows the rail clamp 100 to be moved relative to a patient's location on the table 25.

Rail clamp 100 is further configured to receive multiple modular attachments for use in supporting a patient's arm or other extremity during use. Rail clamp 100 includes a clamp body 120 protruding upwardly from the clamp base 112. Clamp body 120 includes a longitudinal section that is configured to extend generally upwardly away from the rail during use. A longitudinal socket 128 is defined in the rail clamp 100 in some embodiments. Socket 128 is shaped to receive a portion of a modular attachment in the socket.

Figure 2:
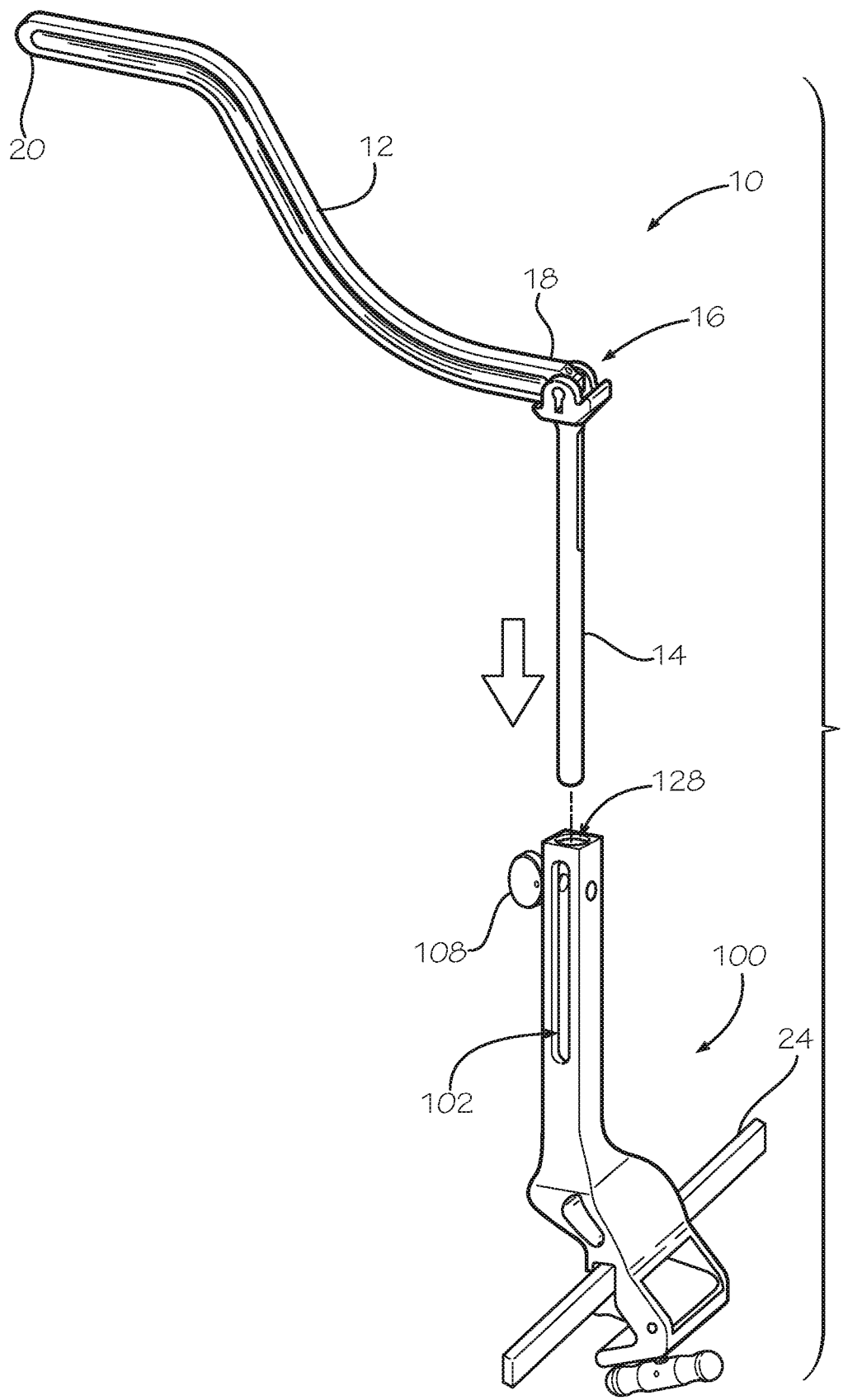
FIG. 2 illustrates a partially exploded perspective view of an embodiment of a rail clamp and arm support in accordance with the present disclosure.

As seen in FIG. 2, one type of modular attachment for installation on rail clamp 100 includes an arm stabilizer, or support arm 10. Support arm 10 includes a stabilizer bar 12 and a base 14. The stabilizer bar 12 is pivotally attached to the base 14 in some embodiments. In alternative embodiments, stabilizer bar 12 and base 14 include a rigid configuration on support arm 10. Base 14 includes a longitudinal shaft in some embodiments. The shaft on base 14 is shaped to be inserted longitudinally in socket 128 on rail clamp 100 in some embodiments. The shaft may form a rod having a round, oval or polygonal cross-sectional profile in various embodiments. The shaft of base 14 is dimensioned to fit in socket 128 on rail clamp 100. The shaft may be loaded into socket 128 in a generally vertical orientation after rail clamp 100 is secured to a rail on a table. Alternatively, the shaft of base 14 may be installed into the socket 128 on rail clamp 100 prior to attachment of rail clamp 100 to the rail on the operating table.

Figure 3:
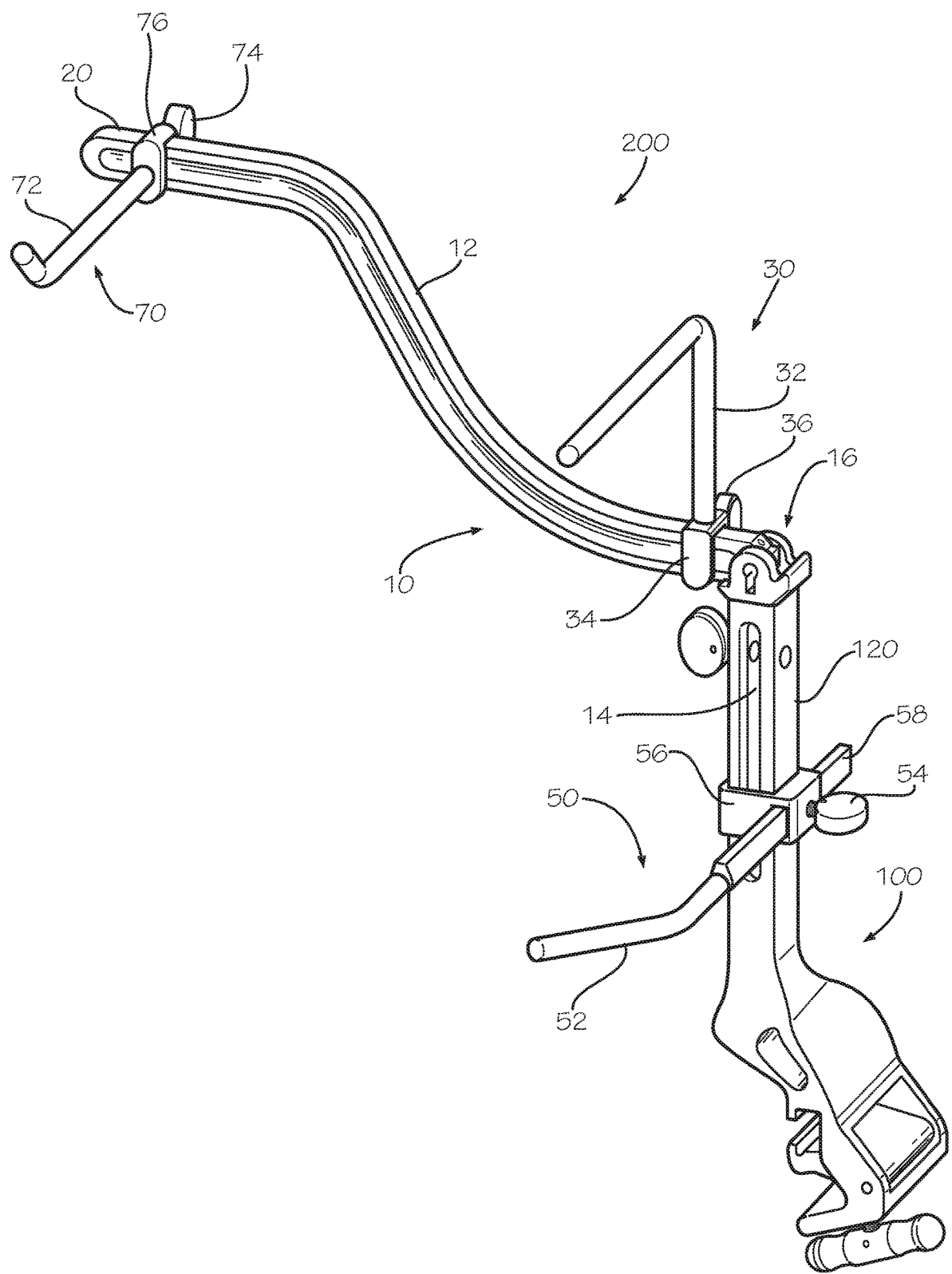
FIG. 3 illustrates a perspective view of an embodiment of an arm positioner device in accordance with the present disclosure.
Figure 4:
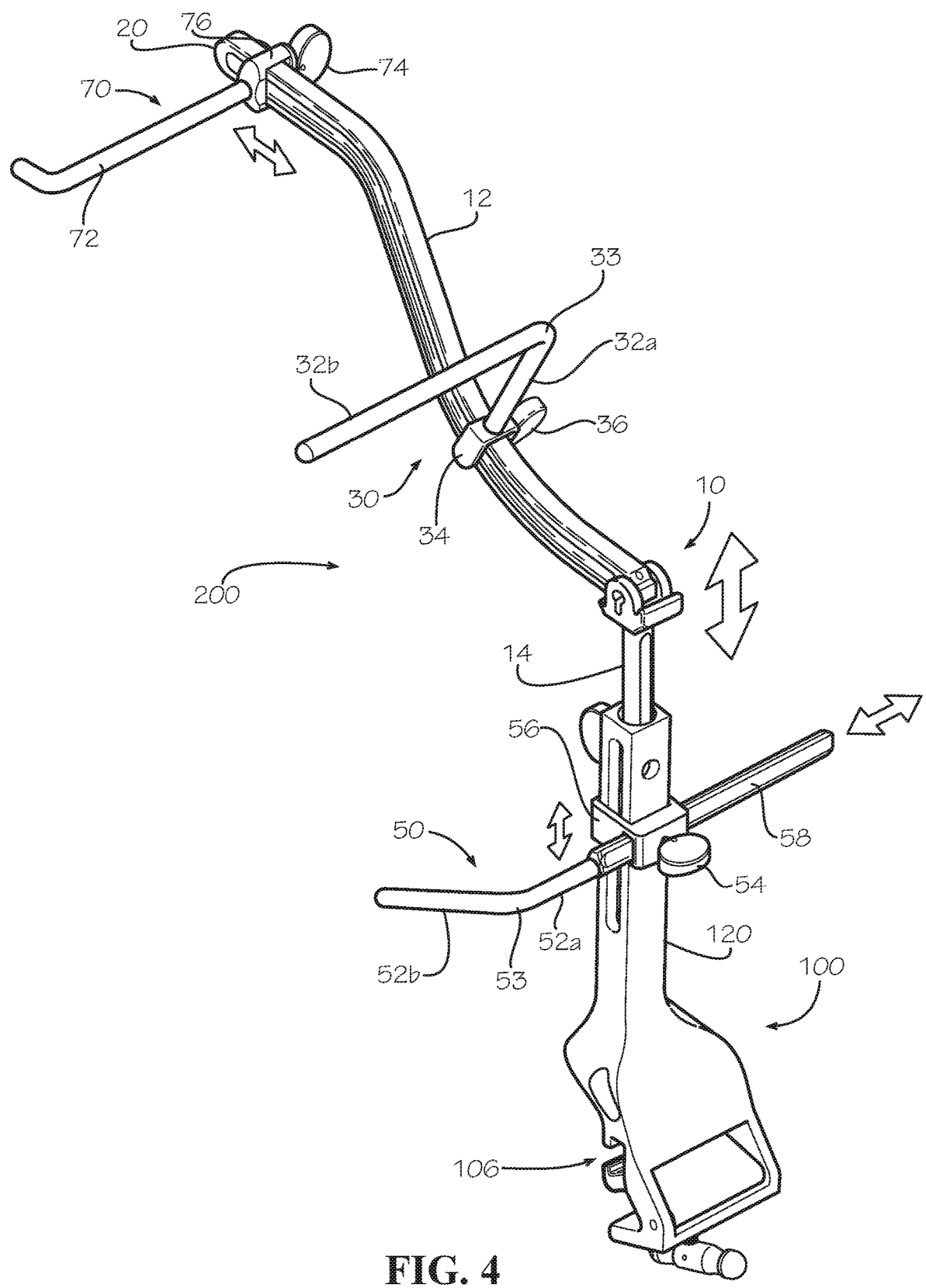
FIG. 4 illustrates a perspective view of an alternative embodiment of an arm positioner device in accordance with the present disclosure.

Base 14 is secured in place on rail clamp 100 using a socket fastener 108 in some embodiments. Socket fastener 108 includes a threaded fastener inserted in a transverse threaded bore in the clamp body 120 on rail clamp 100. Socket fastener 108 may be tightened against a portion of base 14 housed in socket 128 to secure the base 14 in place, as seen in FIG. 3. Base 14 is longitudinally adjustable relative to rail clamp 100 in some embodiments, as seen in FIG. 4. Socket fastener 108 may be loosened, and base 14 may be slid up or down to accommodate patients of different sizes. When a proper position is reached, socket fastener 108 is re-tightened to hold the base 14 in place. The ability to load and unload base 14 into or away from rail clamp 100 in a longitudinal orientation provides an advantage over other loading configurations in some applications because a longitudinal configuration allows displacement of the base 14 substantially parallel to a patient's humeral region without causing the stabilizer bar 12 to laterally interfere with the patient's arm.

Referring further to FIGS. 1-4, rail clamp 100 also includes a clamp groove 102 in some embodiments. Clamp groove 102 generally includes a recess defined on the clamp body 120 forming a channel for attachment of one or more modular components. Clamp groove 102 includes a blind recess in some configurations forming a slight channel for receiving a corresponding structure. The clamp groove 102 allows a modular attachment to be slid along the length of the groove for positioning of the attachment. Alternatively, clamp groove 102 provides a clearance groove that is open to the socket 128 such that the portion of base 14 extending into socket 128 is visible through the clearance in the clamp groove 102. In such configurations, a user may be able to visually inspect the location of base 14 in socket 128. This allows a user to ensure the base is sufficiently installed a proper depth into socket 128 to provide adequate support. If base 14 does not extend far enough into socket 128, support arm 10 may inadvertently become loosened from the rail clamp 100 and allow undesirable motion during use. By providing a clamp groove 102 having a clearance section, it is possible to visually verify the base 14 is located at a proper position in the socket 128. Accordingly, in some embodiments, base 14 has indicia at a predetermined location such that a user may visually inspect the location of base 14 relative to socket 128.

Figure 8:
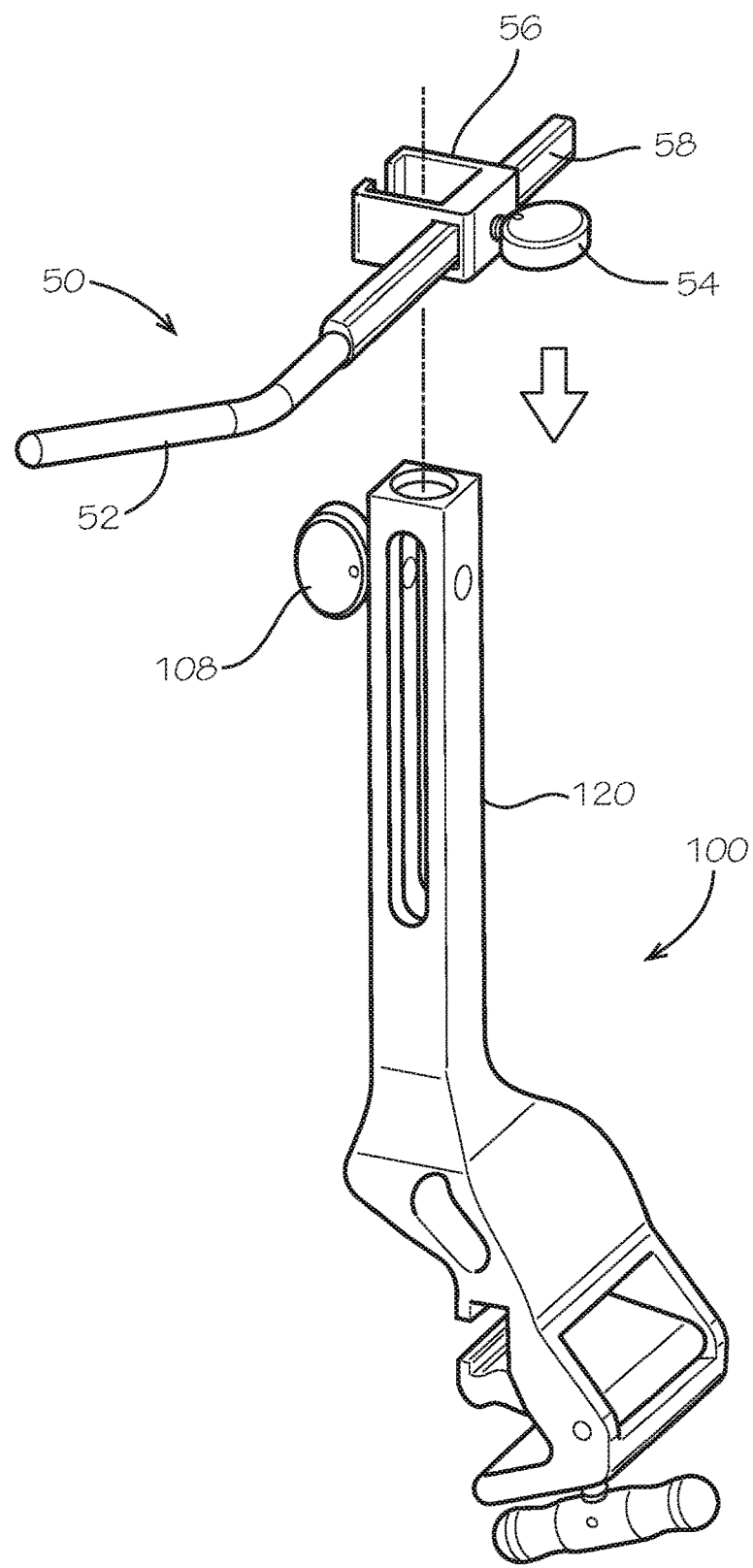
FIG. 8 illustrates a partially exploded perspective view of an embodiment of a rail clamp and humeral support attachment in accordance with the present disclosure.
Figure 9:
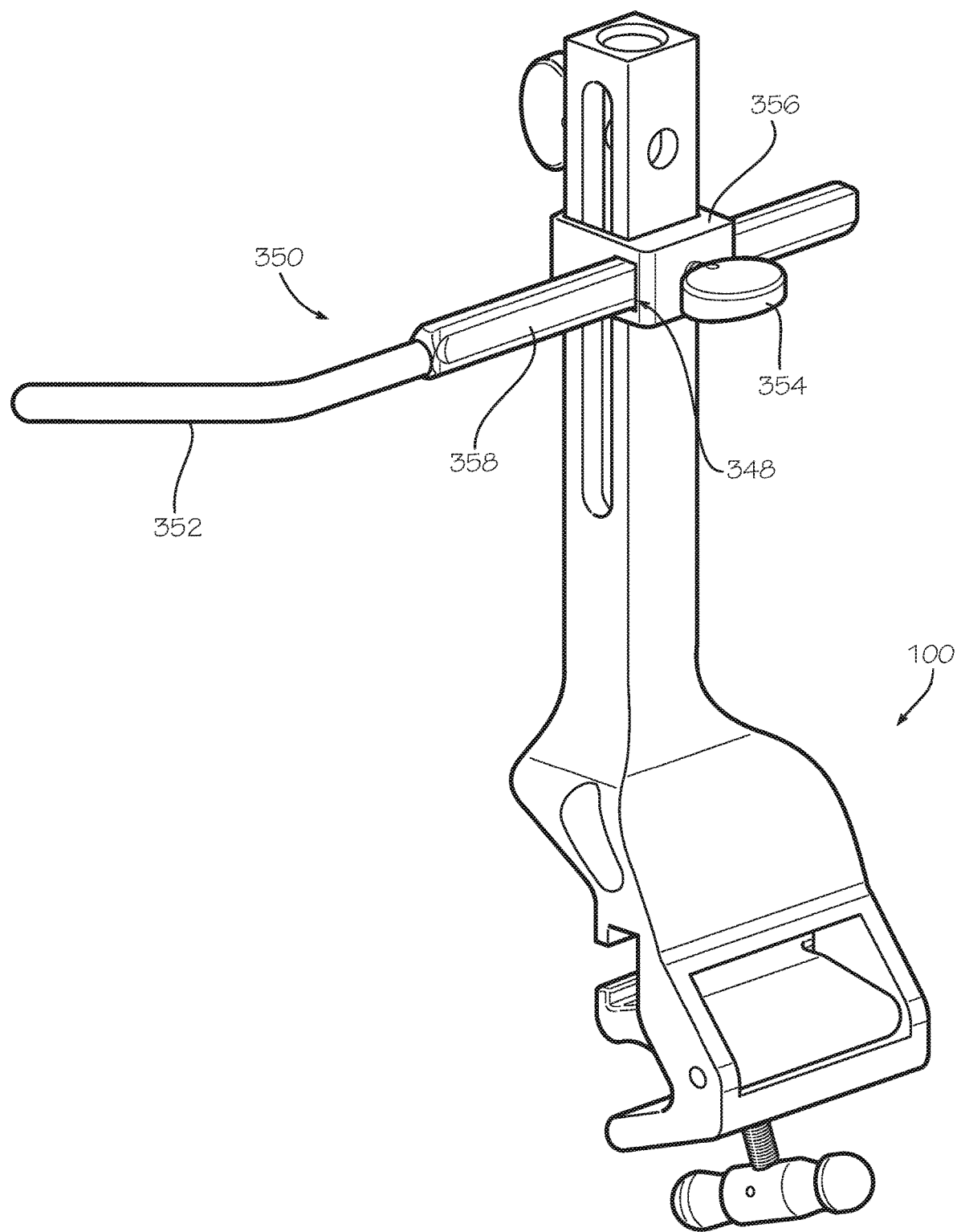
FIG. 9 illustrates a perspective view of the rail clamp and humeral support attachment of FIG. 8 in an assembled state in accordance with the present disclosure.

Clamp body 120 provides a mounting location for one or more modular attachments. As seen in FIGS. 2-4 and FIGS. 8-9, a humeral support attachment 50 is mounted on rail clamp 100 in some embodiments. More specifically, humeral support attachment 50 includes humeral support mount 56 shaped to be installed on rail clamp 100. Humeral support mount 56 may be slid onto clamp body 120 as shown in FIGS. 8-9. A humeral mount fastener 54 is positioned on humeral support mount 56 to secure humeral support attachment 50 at a desired location on rail clamp 100. Humeral mount fastener 54 includes a threaded fastener extending through a corresponding threaded hole in humeral support mount 56. The humeral support mount 56 may be slid up or down along the longitudinal length of clamp body 120 on rail clamp 100 and secured at a desired location using humeral mount fastener 54.

A humeral support arm 52 protrudes from humeral support mount 56 in some embodiments. Humeral support arm 52 extends generally transverse to the longitudinal orientation of rail clamp 100 in some applications. Humeral support arm 52 includes a slide 58 disposed through a humeral mount opening 48 in humeral support mount 56 in some embodiments. Slide 58 is moveable through humeral mount opening 48 to allow the humeral support arm 52 to be selectively repositioned relative to the rail clamp 100. As such, a user may modify the distance the humeral support arm 52 extends from rail clamp 100. This may be advantageous when configuring the device to support patients of different sizes.

As seen in FIG. 4, in some embodiments, humeral support arm includes a first humeral support arm section 52a and a second humeral support arm section 52b separated at a humeral support arm bend 53. The first and second humeral support arm sections are angled at a generally obtuse angle. In some embodiments, this angle is between about 180 degrees and about 140 degrees. The slight angle between these sections provides improved support of the humeral section of the patient's arm during use.

In some embodiments, humeral mount fastener 54 secures the humeral support arm 52 in place by applying force against the slide region 58 of humeral support arm 52 and also secures the humeral support mount 56 in place relative to the rail clamp 100. As seen in FIG. 9, tightening the humeral mount fastener 54 applies force against the slide region 58 on the humeral support arm 52. The applied force presses the other side of the slide region 58 against the surface of the clamp body 120 on the rail clamp 100, thereby securing both the humeral support arm 52 and the humeral support mount 56 in place relative to the rail clamp 100. In some embodiments, the present invention provides a humeral support attachment including a humeral support arm that is moveable in two axes relative to the rail clamp. Specifically, the humeral support arm is vertically moveable along the longitudinal direction of the clamp body and is also moveable transverse to the clamp body in the longitudinal direction of the humeral support arm. This provides an advantage over conventional humeral support devices that may be fixed in place relative to the rail clamp or otherwise limited to adjustment along only one axis.

Referring further to FIGS. 2-4, in further embodiments one or more modular attachments may be secured to the stabilizer bar 12 on support arm 10 to form arm positioner device 200. Stabilizer bar 12 includes a longitudinal bar having a proximal bar end 18 located near base 14 and a distal bar end 20 extending away from base 14. One or more modular attachments may be secured to the stabilizer bar 12 between the proximal and distal bar ends. For example, a wrist support attachment 70 is secured to the stabilizer bar 12 on support arm 10 in some embodiments. Wrist support attachment 70 provides a structure for supporting a wrist, forearm or hand region on a patient during use. Wrist support attachment includes a wrist support mount 76 and a wrist support bar 72 protruding from the wrist support mount 76 in a direction away from the stabilizer bar 12. Wrist support mount 76 engages the stabilizer bar 12 and includes a wrist support fastener 74 for securing the wrist support attachment 70 to the stabilizer bar 12 in some embodiments. Wrist support fastener 74 includes a threaded fastener in some embodiments. Wrist support fastener 74 applies a force against the side of the stabilizer bar 12 to secure the wrist support attachment 70 in place. Wrist support attachment 70 may be repositioned along the length of the stabilizer bar 12 by loosening the wrist support fastener 74, repositioning the wrist support mount 76 to a desired location along the length of stabilizer bar 12, and then retightening wrist support fastener 74. The ability to reposition the wrist support attachment 70 relative to the stabilizer bar 12 provides an advantage over other supports that are fixed in place.

As seen in FIG. 4, in some embodiments, wrist support bar 72 includes an angled end to further support a patient's wrist, hand or forearm and to keep the patient's extremity from inadvertently sliding off the end of the wrist support bar 72. Additionally, a mounting groove may be defined in the stabilizer bar 12 along the length of the stabilizer bar 12. One or more structures on the wrist support mount 76 extend at least partially into the mounting groove on the stabilizer bar 12. As such, the mounting groove in the stabilizer bar operates as a track along which the wrist support mount 76, or any other modular attachment, may slide during adjustment of the attachment.

Figure 10:
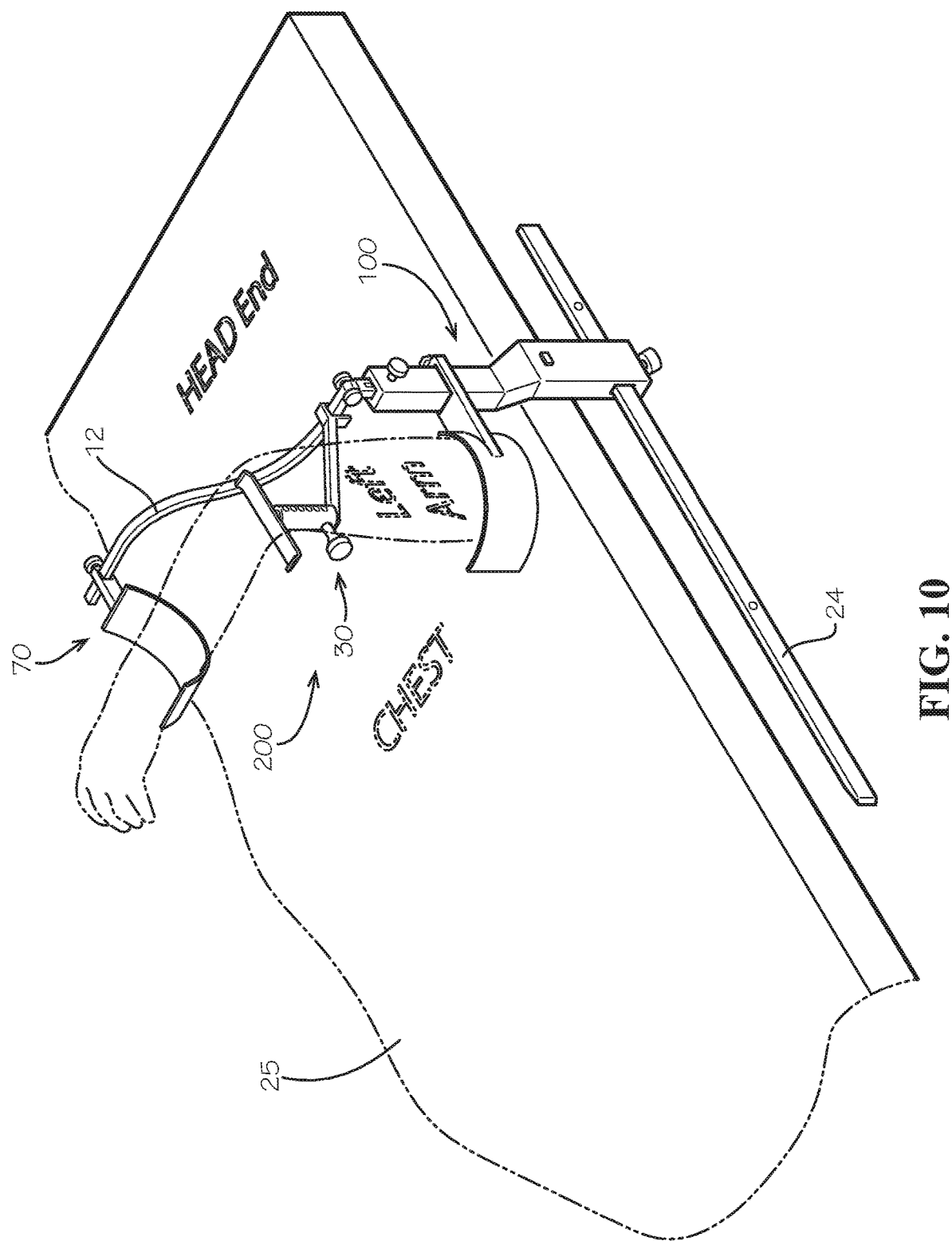
FIG. 10 illustrates a perspective view of an embodiment of an arm positioner arranged to support a patient's arm in a supine position on a patient table in accordance with the present disclosure.

Referring further to FIGS. 3-4, another type of attachment known as a reducer attachment 30 may be positioned on the stabilizer bar 12. Reducer attachment 30 provides structural support for a patient's humeral region, elbow, or forearm during use. In some applications, a reducer support arm 32 extends from a reducer mount 34 on the reducer attachment. Reducer support arm 32 may be located near a patient's elbow joint, as seen in FIG. 10, when a patient is lying in a supine position on an operating table. The reducer support arm 32 supports an underside portion of a patient's arm and provides a reaction structure against which a physician may apply force during an operation on the patient's arm or elbow.

Referring further to FIG. 4, reducer attachment 30 includes a generally L-shaped reducer support arm 32 in some embodiments including a first reducer support arm section 32*a* and a second reducer support arm section 32*b* oriented at an angle relative to the first reducer support arm section 32*a*. These two sections join at a reducer attachment bend 33 and form a substantially right angle in some embodiments. The second reducer support arm section 32*b* extends away from the stabilizer bar 12 and provides support to the user's arm.

The reducer attachment 30 includes a reducer mount 34 that engages the stabilizer bar 12. A reducer fastener 36 on the reducer mount 34 provides a force against the stabilizer bar 12 to secure the reducer attachment 30 in position. Reducer fastener 36 includes any suitable fastener such as a threaded fastener for applying force against the stabilizer bar 12. A user may adjust the position of the reducer attachment 30 on the stabilizer bar 12 by loosening the reducer fastener 36, repositioning the reducer attachment at a desired location along the length of the stabilizer bar 12, and then retightening the reducer fastener 36. In some embodiments, the reducer fastener 36 engages a mounting groove on the stabilizer bar 12, where the mounting groove operates as a track along which the reducer mount 34 may be slid for positioning the reducer attachment 30.

The reducer attachment 30 may be used on the arm positioner device 200 as the only modular attachment. For example, in some embodiments, the arm positioner device 200 includes only the rail clamp 100, the support arm 10 and the reducer attachment 30. In other embodiments, arm positioner device 200 includes only the rail clamp 100, and humeral support attachment 50, as seen in FIGS. 8-9. In further embodiments, the arm positioner device 200 includes only the rail clamp 100, support arm 10, humeral support attachment 50, and wrist support attachment 70. In additional embodiments, the arm positioner device 200 includes only the rail clamp 100, support arm 10, and wrist support attachment 70. In further embodiments, the arm positioner device 200 includes only the rail clamp 100, support arm 10, wrist support attachment 70, and reducer attachment 30. In yet other embodiments, the arm positioner device 200 includes the rail clamp 100, support arm 10, wrist support attachment 70, humeral support attachment 50 and reducer attachment 30.

Figure 5:
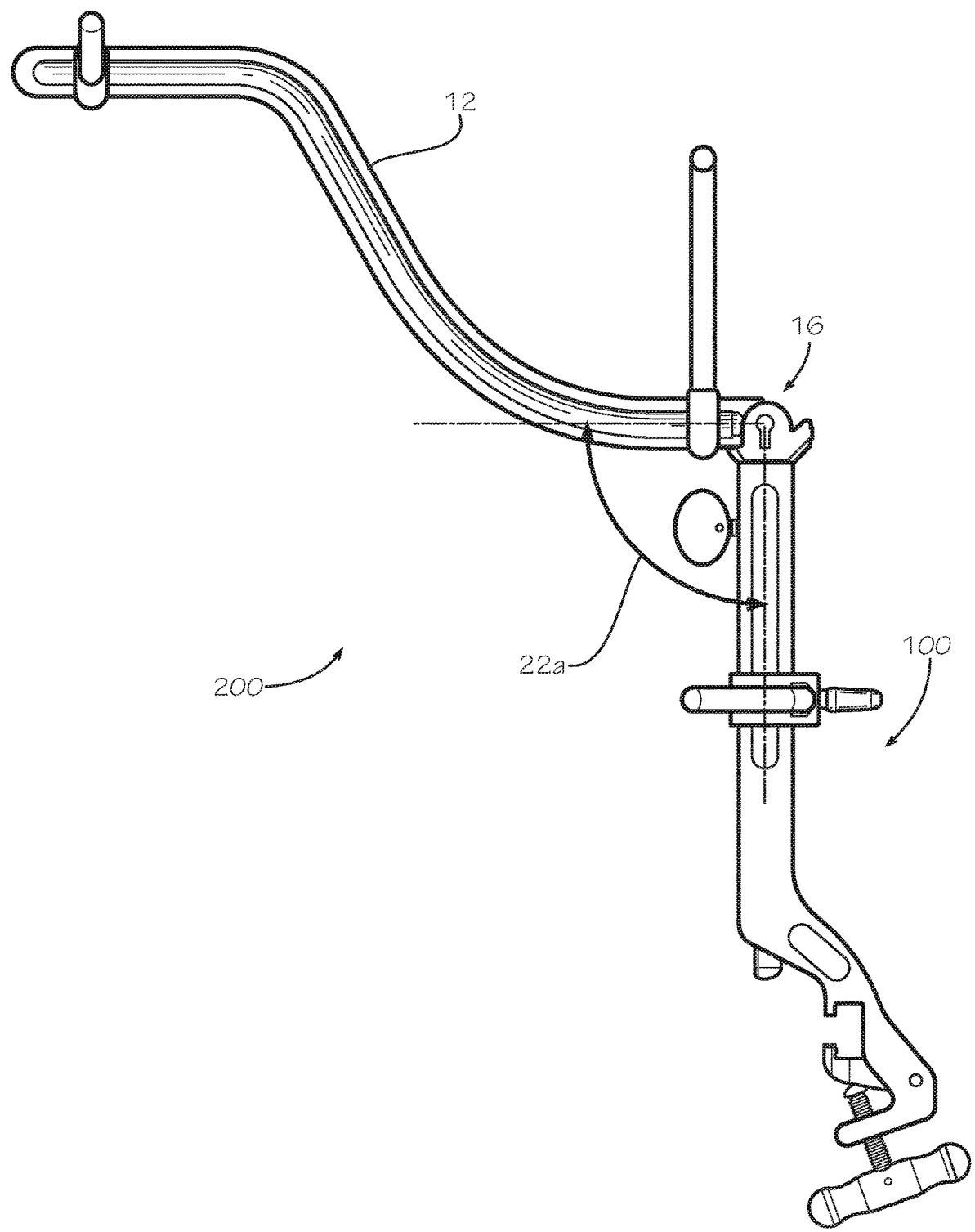
FIG. 5 illustrates a side elevation view of an embodiment of an arm positioner device with a support arm in a first angular position relative to the rail clamp in accordance with the present disclosure.
Figure 6:
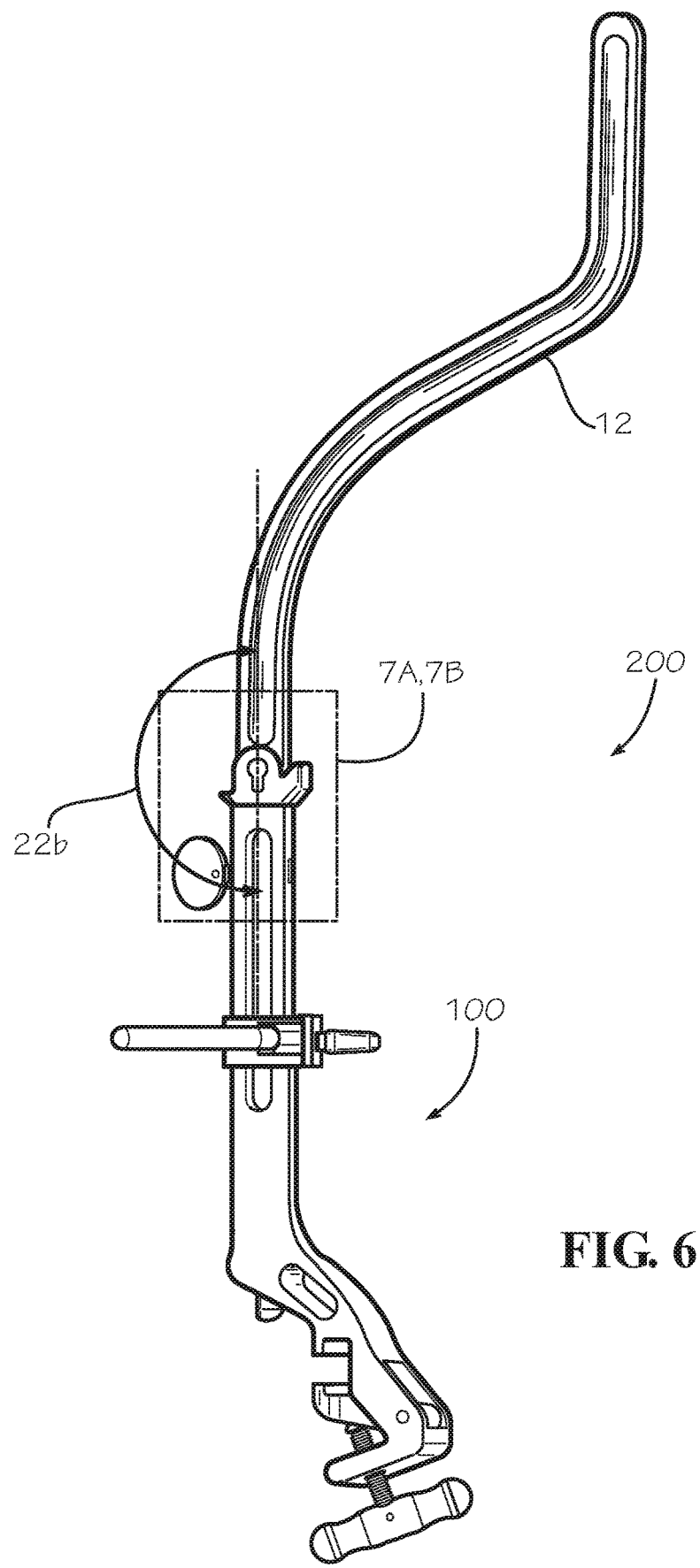
FIG. 6 illustrates a side elevation view of an alternative embodiment of an arm positioner device with a support arm in a second angular position relative to the rail clamp in accordance with the present disclosure.

Referring further to FIGS. 5-7B, in some embodiments the stabilizer bar 12 is angularly moveable relative to the base 14. As such, stabilizer bar 12 is also angularly moveable relative to rail clamp 100 when base 14 is installed on the rail clamp. As seen in FIG. 5, stabilizer bar 12 may be oriented relative to rail clamp 100 at a first angle 22*a*. The first angle may be approximately ninety degrees in some embodiments. A first angle stop 78, shown in FIG. 7A, on support arm 10 provides an angular stop for stabilizer bar 12. Stabilizer bar 12 is attached to base 14 at a base hinge 16 in some embodiments. Stabilizer bar 12 may be angularly rotated back as shown in FIG. 6 to a second angle greater than ninety degrees.

Figure 7A:
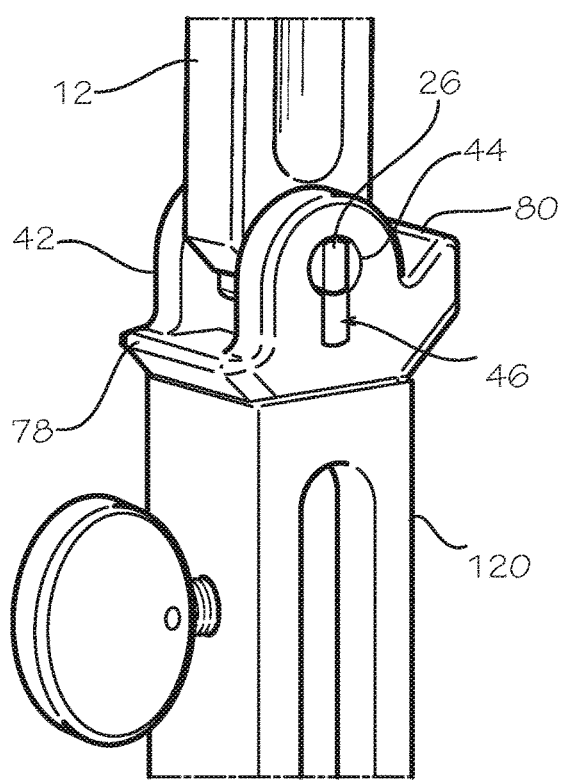
FIG. 7A illustrates a detail perspective view of Section 7A of the embodiment of an arm positioner device from FIG. 6.
Figure 7B:
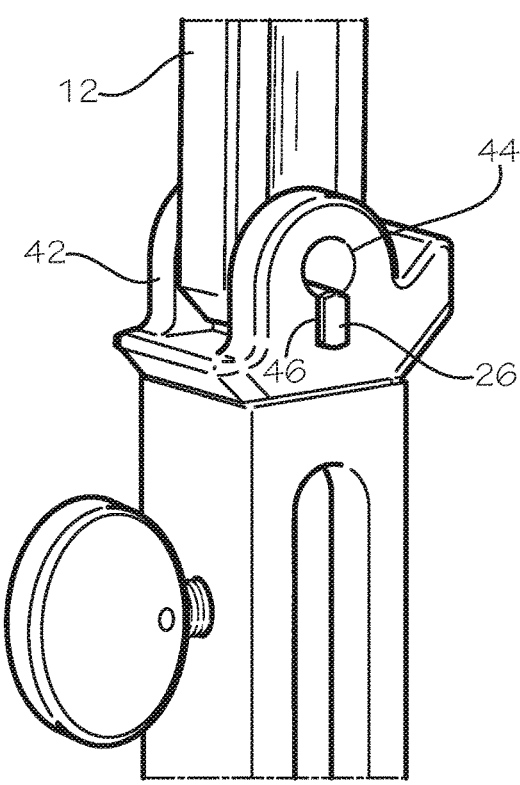
FIG. 7B illustrates a detail perspective view of Section 7B of the embodiment of an arm positioner device from FIG. 6.

In some embodiments, support arm 10 includes an angular lock to secure stabilizer bar 12 at a desired angle. For example, as seen in FIGS. 7A and 7B, a base head 42 is positioned on base 14 in some embodiments. Base head 42 includes a pivot opening 44. A locking pin 26 attached to stabilizer bar 12 extends transversely through and is rotatable in pivot opening 44. A locking slot 46 adjoins and is open to pivot opening 44. Locking pin 26 includes a substantially flat dimension shaped to be received in locking slot 46. Locking pin 26 may slide locking slot 46, as seen in FIG. 7B, when stabilizer arm 12 is positioned at a corresponding angular position. In some applications, the angular lock is configured to selectively lock stabilizer bar 12 in a substantially vertical configuration, as seen in FIG. 6. When a user desires to unlock the angular lock, the stabilizer bar 12 may simply be lifted up to disengage locking pin 26 from locking slot 46, thereby allowing free rotation of locking pin 26 in pivot opening 44.

In some applications, it is desirable to provide a back angular stop on support arm 10 such that stabilizer bar 12 does not rotate too far away from the patient during use. As such, a second angular stop 80 is positioned on base head 42 in some embodiments. Second angular stop allows support arm 10 to be rotated away from a patient when not in use.

Figure 11:
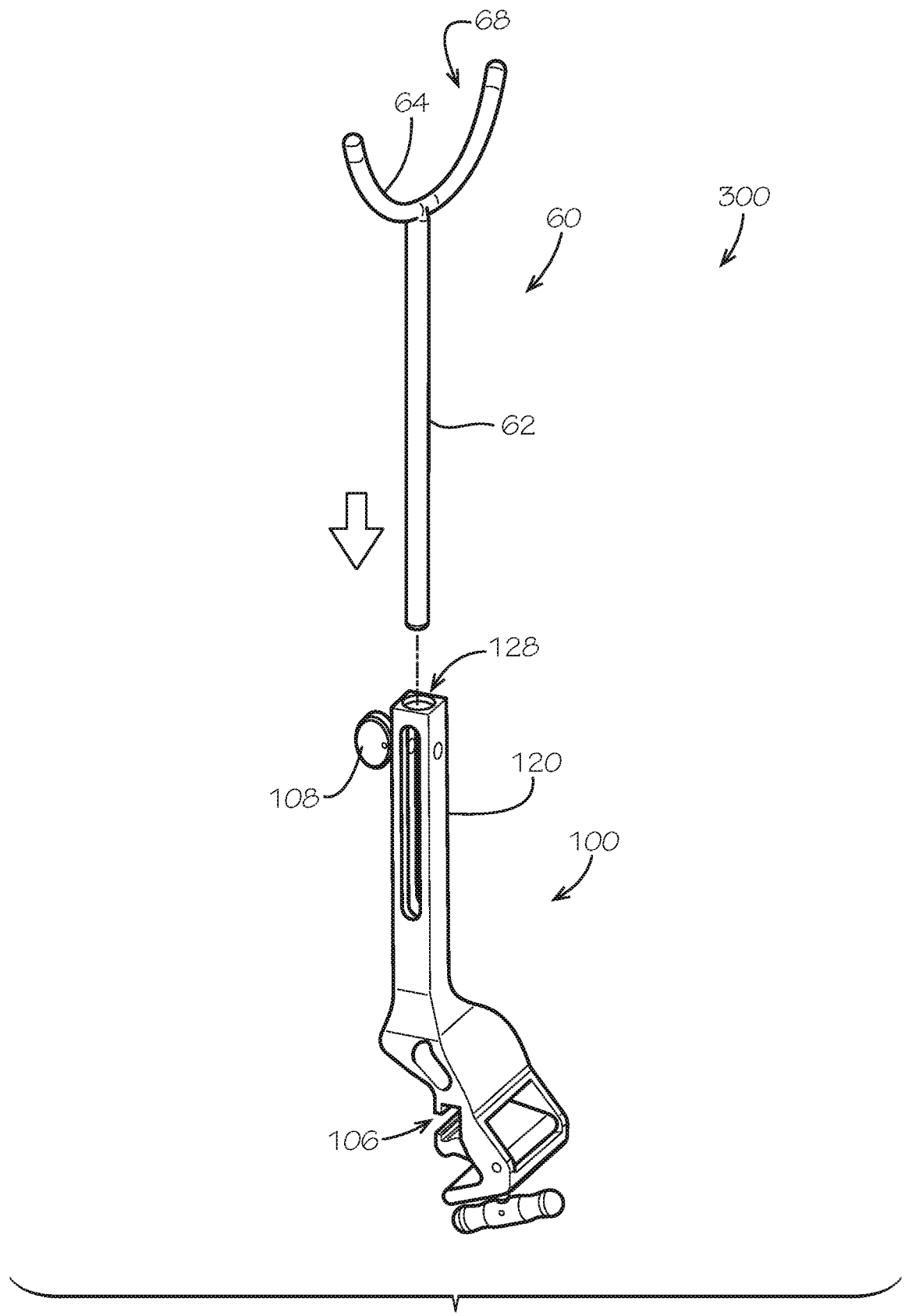
FIG. 11 illustrates a partially exploded perspective view of an embodiment of a lateral positioner including a rail clamp and lateral brace in accordance with the present disclosure.
Figure 12:
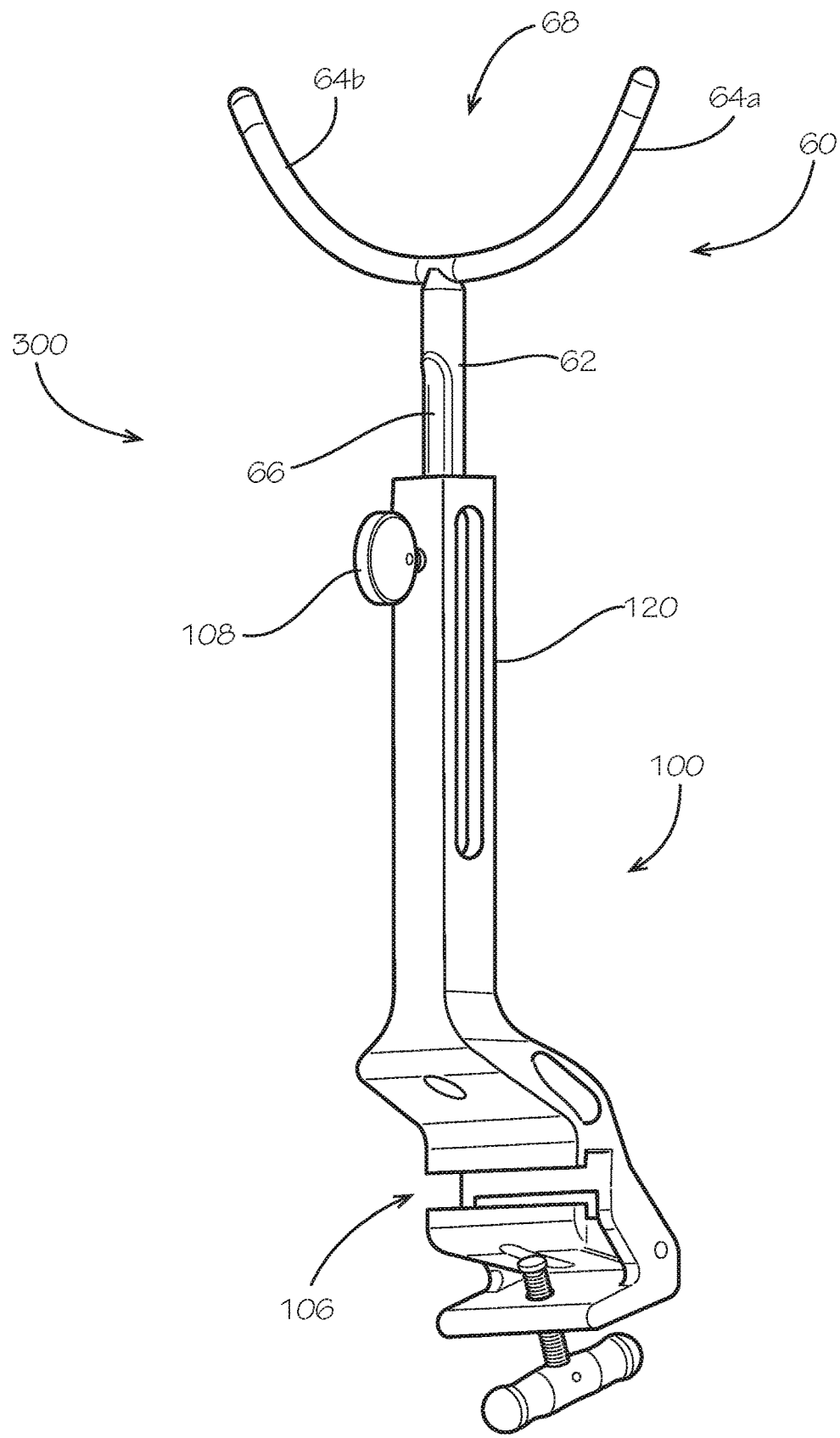
FIG. 12 illustrates a perspective view of the rail clamp and lateral positioner of FIG. 11 in an assembled state in accordance with the present disclosure.
Figure 13:
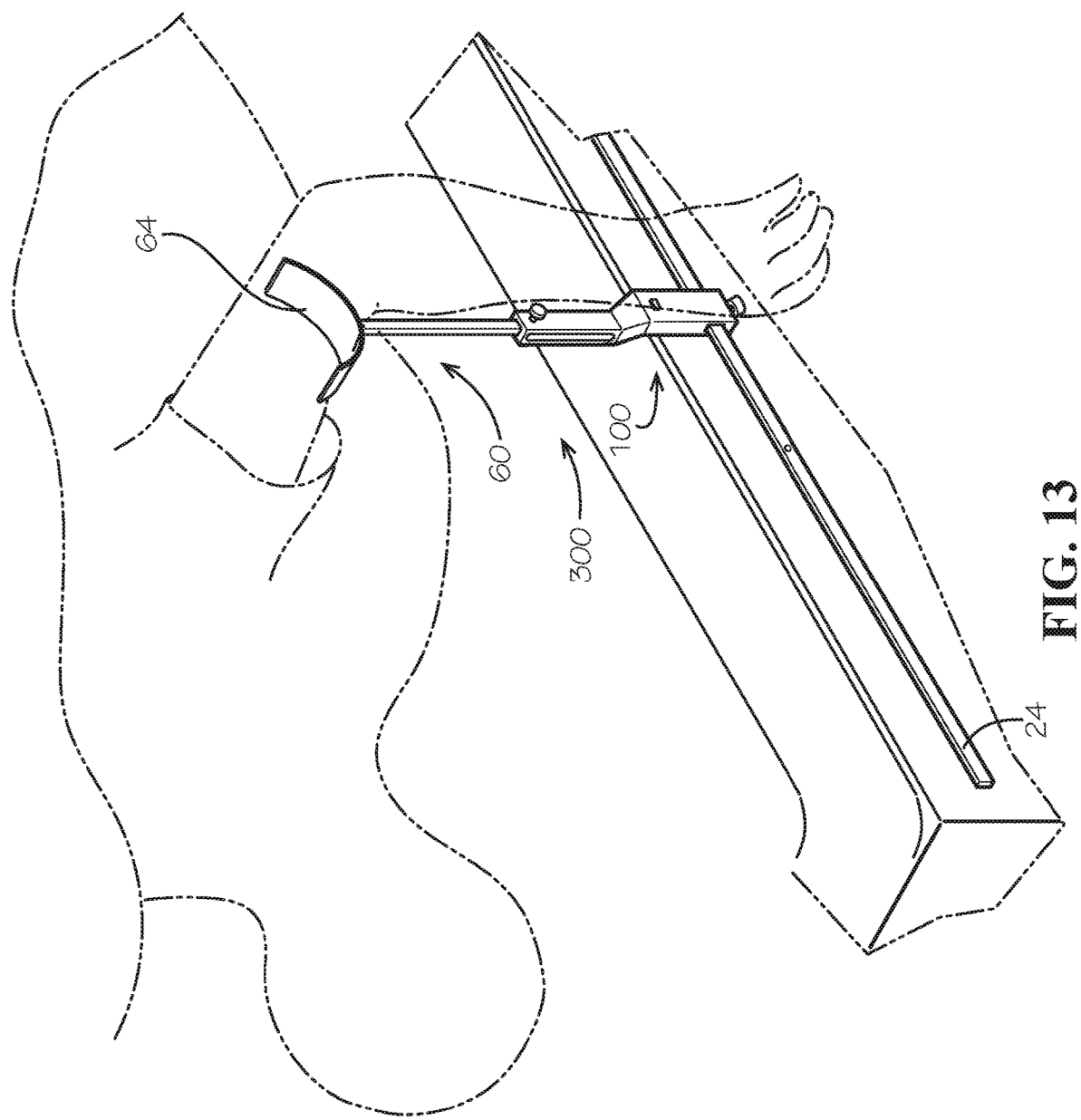
FIG. 13 illustrates a perspective view of an embodiment of a lateral positioner device including a rail clamp and a lateral positioner arranged to support a patient's arm in a face down prone or lateral position on a patient table in accordance with the present disclosure.

Referring further to FIGS. 11-13, additional embodiments of the present invention provide a lateral positioner device that may be used to support a patient's arm in a face down or prone position or in a lateral position. An advantageous feature of the present invention is the ability to use the rail clamp 100 interchangeably with either an arm positioner device 200, as shown in FIGS. 2-6 and with a lateral positioner device 300, as shown in FIGS. 11-13. Lateral positioner device 300 includes a rail clamp 100 as described above. A lateral brace 60 is securable to the rail clamp 100 to provide support to a patient's arm in a prone position, as seen in FIG. 13, or in a lateral position. Lateral brace 60 includes a longitudinal post 62 shaped to be inserted longitudinally in socket 128 on rail clamp 100. Lateral support arms 64 extend from post 62 at a T-shaped junction in some embodiments. First and second lateral support arms 64*a*, 64*b* intersect at post 62 and generally extend away from post 62 at an upward angle, as seen in FIG. 12. A brace recess 68 is defined between first and second lateral support arms 64*a*, 64*b*. A patient's arm is located in the brace recess 68 during an operation. Lateral brace 60 may support a patient's humeral region along the bicep or may engage the patient at or near the elbow joint.

In some embodiments, lateral brace 60 has an adjustable height such that the brace may be repositioned relative to rail clamp 100. For example, as seen in FIG. 12, post 62 is longitudinally adjustable in socket 128 on rail clamp 100. Socket fastener 108 may be tightened against post 62 to secure lateral brace 60 at a desired height. To adjust the height of lateral brace 60, a user may loosen socket fastener 108, reposition post 62, and then retighten socket fastener 108. In some embodiments, post 62 includes a substantially flat surface 66 to provide enhanced application of force from socket fastener 108. Additionally, in some embodiments, flat surface 66 prevents inadvertent rotation of post 62 when engaged by socket fastener 108.

Figure 14:
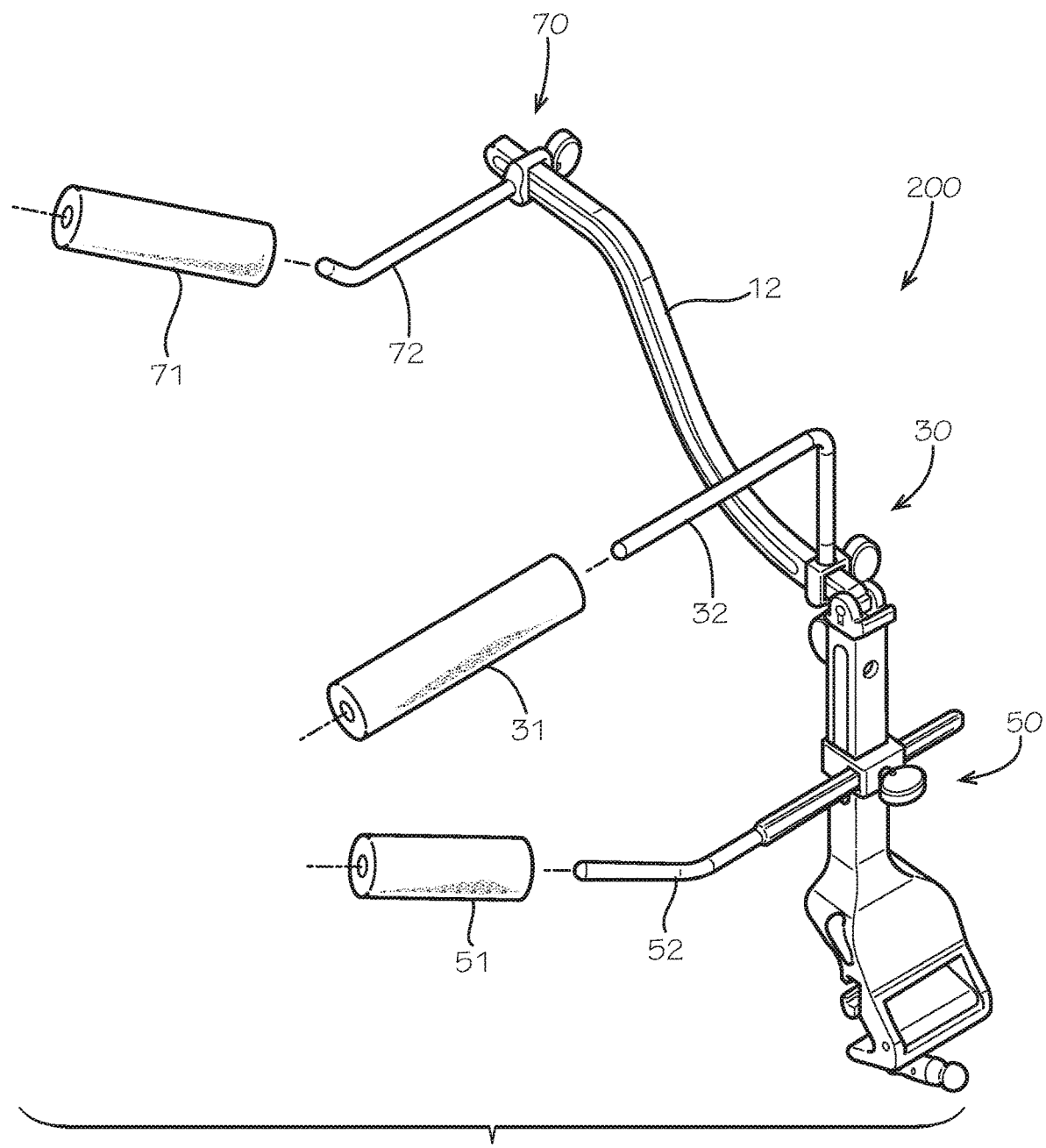
FIG. 14 illustrates a partially exploded perspective view of an embodiment of an arm positioner and pad attachments in accordance with the present disclosure.
Figure 15:
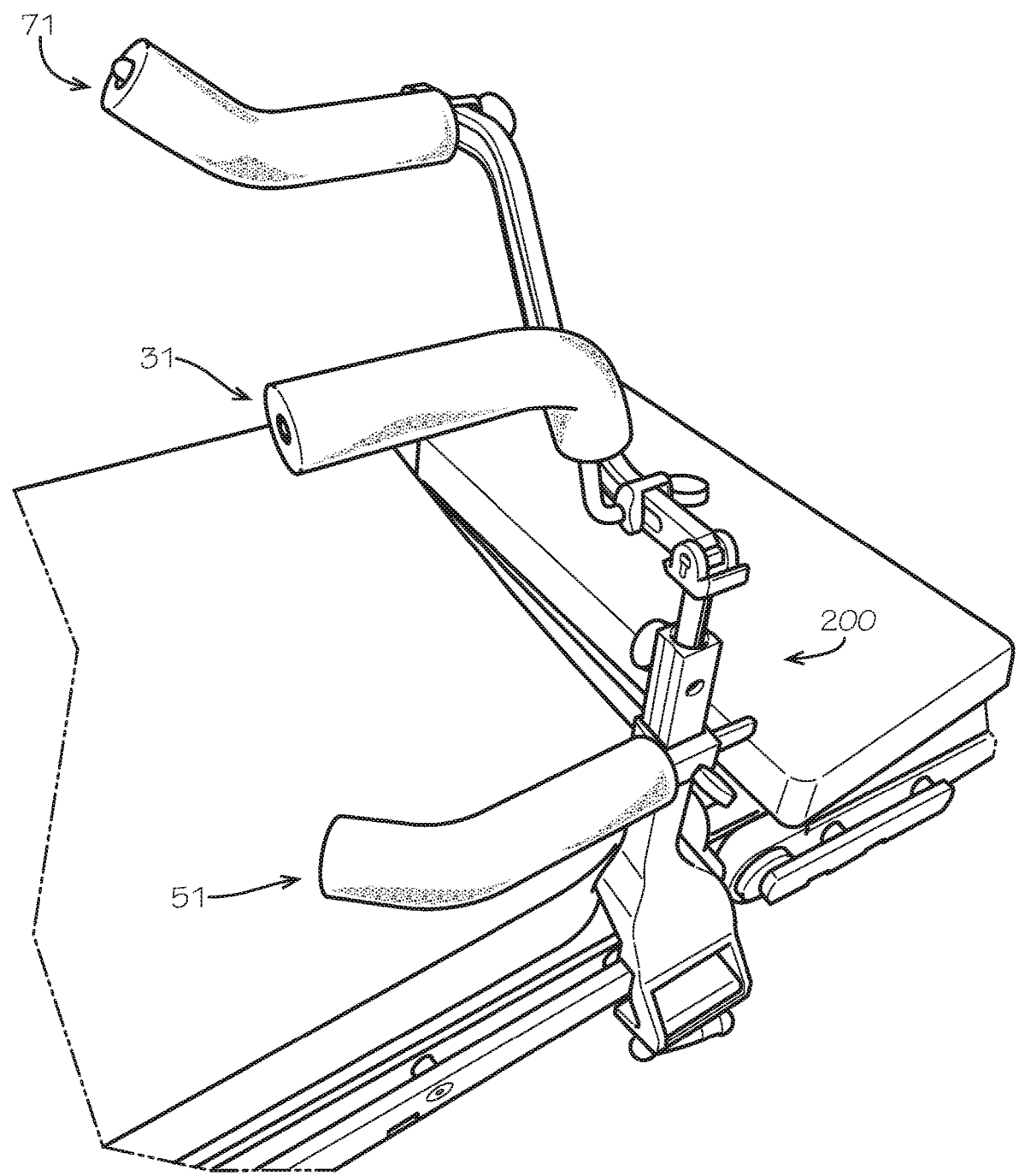
FIG. 15 illustrates a perspective view of an embodiment of an arm positioner with pad attachments installed in accordance with the present disclosure.
Figure 16:
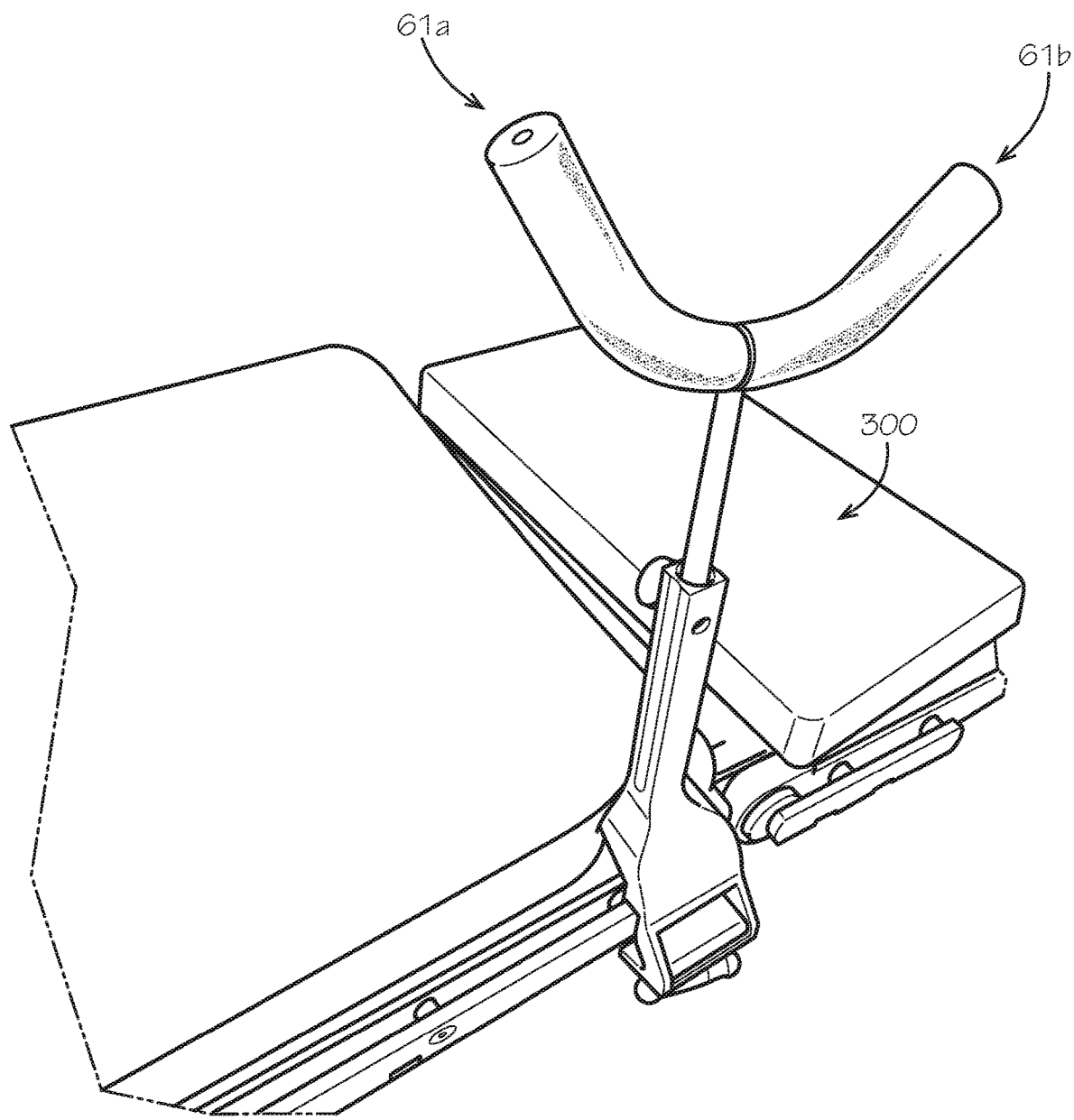
FIG. 16 illustrates a perspective view of an embodiment of a lateral positioner device with pad attachments installed in accordance with the present disclosure.

Referring further to FIGS. 14-16, various pad attachments may be positioned on each modular attachment to provide a padded interface between the attachment and a user's arm. For example, as seen in FIG. 14, humeral support attachment 50 includes a humeral support arm 52. A humeral support pad 51 includes an elongated pad having a hollow interior aperture shaped to receive the humeral support arm 52. In some embodiments, humeral support pad 51 includes a generally cylindrical hollow tubular shape. As such, the humeral support pad 51 may be slid directly onto the humeral support arm 52, as seen in FIG. 15. Humeral support pad 51 includes pad material such as but not limited to an open-cell or closed-cell foam material, foam rubber, polyethylene padding, latex padding, EVA padding, or any other suitable padding material. Humeral support pad 51 includes a disposable pad that may be discarded after use in some applications.

Referring further to FIG. 14, reducer attachment 30 includes a reducer support arm 32. A reducer support pad 31 includes an elongated pad having a hollow interior aperture shaped to receive the reducer support arm 32. In some embodiments, reducer support pad 31 includes a generally cylindrical hollow tubular shape. As such, the reducer support pad 31 may be slid directly onto the reducer support arm 32, as seen in FIG. 15. Reducer support pad 31 includes pad material such as but not limited to an open-cell or closed-cell foam material, foam rubber, polyethylene padding, latex padding, EVA padding, or any other suitable padding material. Reducer support pad 31 includes a disposable pad that may be discarded after use in some applications.

Referring further to FIG. 14, wrist support attachment 70 includes a wrist support arm 72. A wrist support pad 71 includes an elongated pad having a hollow interior aperture shaped to receive the wrist support arm 72. In some embodiments, wrist support pad 71 includes a generally cylindrical hollow tubular shape. As such, the wrist support pad 71 may be slid directly onto the wrist support arm 72, as seen in FIG. 15. Wrist support pad 71 includes pad material such as but not limited to an open-cell or closed-cell foam material, foam rubber, polyethylene padding, latex padding, EVA padding, or any other suitable padding material. Wrist support pad 51 includes a disposable pad that may be discarded after use in some applications.

Referring further to FIG. 12 and FIG. 16, lateral positioner device 300 may also include one or more pads on first and second lateral support arms 64a, 64b. For example, a first lateral support arm pad 61a is positioned on first lateral support arm 64a, and a second lateral support arm pad 61b is positioned on second lateral support arm 64b. Each lateral support arm pad 61a, 61b includes an elongated pad having a hollow interior aperture shaped to receive its corresponding lateral support arm. In some embodiments, each lateral support arm pad includes a generally cylindrical shape. Each lateral support arm pad may be slid directly onto its corresponding lateral support arm, as seen in FIG. 16. Each lateral support arm pad includes pad material such as but not limited to an open-cell or closed-cell foam material, foam rubber, polyethylene padding, latex padding, EVA padding, or any other suitable padding material. Each lateral support arm pad includes a disposable pad that may be discarded after use in some applications.

Referring further to FIGS. 17-19, a pad kit apparatus 400 is provided in some embodiments. Pad kit apparatus 400 includes a package including first, second and third pads 402a, 402b, 402c housed within a sealed enclosure 404. Enclosure 404 provides a sealed, sterile package for first, second and third pads. A user may open enclosure 404 to access the pads. First and second straps 406, 408 are included in the package in some embodiments. Each strap includes a hook-and-loop fabric in some embodiments to provide a fastener for securing a portion of a patient's body to one of the first, second and third pads. Each strap is dimensioned to extend around a patient's arm, hand or wrist and also around one of the first, second and third pads in some embodiments.

In some embodiments, each of the first, second and third pads include substantially identical dimensions. As such, each pad is generally interchangeable and may be used as a humeral support pad 51, a reducer support pad 31, a wrist support pad 71, or a lateral support arm pad 61. In some embodiments, each pad includes an axial length between about ten centimeters and about thirty centimeters. In further embodiments, each pad includes an axial length of about twenty centimeters. Each pad also includes an outer diameter of between about two and about six centimeters in some embodiments. In further embodiments, each pad includes an outer diameter of about four centimeters. Additionally, each pad includes an axial passage defined through the axial length of the pad. The axial passage is dimensioned to receive one or more support bars such as wrist support bar 72, humeral support bar 52 or reducer support bar 32. In some embodiments, each axial passage includes an inner diameter of between about 0.5 centimeters and about 1.5 centimeters. In further embodiments, the axial passage in each pad includes an inner diameter of about 1.1 centimeters. In some embodiments, the axial passage in each pad includes an inner diameter equal to or less than the outer diameters of the wrist support bar 72, humeral support bar 52, and reducer support bar 32 to provide a closer or interference fit.

The pad kit apparatus 400 may be provided as an accessory package for use with an arm positioner device or lateral positioner device in accordance with the present disclosure. The pad kit apparatus 400 is entirely disposable after use in some embodiments. Each pad in the pad kit apparatus 400 is configured for use specifically on one of the wrist support bar 72, humeral support bar 52, reducer support bar 32, or lateral support bar.

As seen in FIG. 18, package 404 includes two sheets joined together around the perimeter to form an enclosure for the first, second and third pads and first and second straps. The top sheet 404a includes a transparent material in some embodiments. The backing sheet 404b includes a reinforced paper or polymer backing in some embodiments.

Thus, although there have been described particular embodiments of the present invention of a new and useful Lateral Positioner for Elbow Surgery, it is not intended that such references be construed as limitations upon the scope of this invention except as set forth in the following claims.

The invention claimed is:

1. A lateral arm positioner apparatus for mounting on a rail of a table and for supporting a patient's arm when the patient is lying in a prone or lateral position on the table, the apparatus comprising:
   a rail clamp having a clamp base securable to the rail and having a clamp body protruding upward from the clamp base;
   a longitudinal socket defined in the clamp body;
   an arm brace including a longitudinal post shaped to be received in the longitudinal socket of the clamp body; and
   at least one lateral support arm extending from the longitudinal post positioned to support the patient's arm, wherein the at least one lateral support arm extends away from the rail clamp at an upward angle away from the rail clamp, wherein
   the at least one lateral support arm includes a first lateral support arm and a second lateral support arm, and
   the first and second lateral support arms define a brace recess between the first and second lateral support arms, the brace recess positioned to support a humeral region of the patient.

2. The apparatus of claim 1, wherein the arm brace has an adjustable height relative to the rail clamp.

3. The apparatus of claim 2, further comprising:
   a socket disposed on the rail clamp; and
   a socket fastener, wherein the socket fastener may be tightened and loosened relative to the rail clamp such that the socket fastener is tightened against the longitudinal post.

4. The apparatus of claim 3, wherein:
   the socket disposed on the rail clamp includes a transverse threaded bore extending from an exterior of the clamp body to the longitudinal socket; and
   the socket fastener includes a threaded fastener inserted into the socket disposed on the rail clamp, wherein the socket fastener may be tightened against the longitudinal post.

5. The apparatus of claim 4, wherein:
   the longitudinal post includes a substantially flat surface; and
   the threaded fastener selectably engages the substantially flat surface when tightened against to-the longitudinal post.

6. The apparatus of claim 1, wherein the longitudinal post is selectively moveable relative to the rail clamp.

7. The apparatus of claim 6, further comprising a removable foam pad positioned on the lateral support arm.

8. The apparatus of claim 6, wherein the longitudinal post is selectively moveable relative to the clamp body of the rail clamp.

9. The apparatus of claim 1, wherein the clamp base is offset from the clamp body.

10. The apparatus of claim 1, wherein the at least one lateral support arm extends from a T-shaped junction of the longitudinal post.

11. A lateral arm positioner apparatus for mounting on a rail of a table and for supporting a patient's arm when the patient is lying in a prone or lateral position on the table, the apparatus comprising:
   a rail clamp including
      a clamp base securable to the rail,
      a rail clamp fastener disposed on the clamp base, and
      a clamp body protruding upward from the clamp base;
   a longitudinal socket defined in the clamp body; and
   an arm brace including
      a longitudinal post shaped to be received in the longitudinal socket of the clamp body,
      a T-shaped junction disposed at an end of the longitudinal post,
      a first lateral support arm disposed on the T-shaped junction and extending away from the longitudinal post, and
      a second lateral support arm disposed on the T-shaped junction and extending away from the longitudinal post,
      wherein the first and second lateral support arms extend away from the rail clamp at an upward angle away from the rail clamp.

12. The apparatus of claim 11, wherein the longitudinal post is selectively moveable relative to the rail clamp.

13. The apparatus of claim 11, further comprising:
   a first removable foam pad positioned on the first lateral support arm; and
   a second removable foam pad positioned on the second lateral support arm.

14. The apparatus of claim 11, wherein the first and second lateral support arms define a brace recess between the first and second lateral support arms positioned to support a humeral region of the patient.

15. The apparatus of claim 11, further comprising:
   a socket disposed on the rail clamp; and
   a socket fastener, wherein the socket fastener may be tightened and loosened relative to the rail clamp such that the socket fastener is tightened against the longitudinal post.

16. The apparatus of claim 15, wherein:
   the socket disposed on the rail clamp includes a transverse threaded bore extending from an exterior of the clamp body to the longitudinal socket; and
   the socket fastener includes a threaded fastener inserted into the socket disposed on the rail clamp, wherein the socket fastener may be tightened against the longitudinal post.

17. A method of supporting a supporting patient's arm when the patient is lying in a prone or lateral position on a table, comprising:
   securing a clamp base of a rail clamp to a rail of the table, wherein a longitudinal socket is defined in a clamp body of the rail clamp;
   inserting a longitudinal post into the longitudinal socket of the rail clamp, wherein the longitudinal post is defined on an arm brace having at least one lateral support arm; and
   supporting the patient's arm on the at least one lateral support arm, wherein the at least one lateral support arm extends away from the rail clamp at an upward angle away from the rail clamp.

18. The method of claim 17, further comprising moving the longitudinal post relative to the rail clamp.

19. The method of claim 18, further comprising tightening a socket fastener relative to the rail clamp such that the socket fastener is tightened against the longitudinal post.

* * * * *